(12) United States Patent
Collerais

(10) Patent No.: US 11,642,154 B2
(45) Date of Patent: May 9, 2023

(54) FIXATOR FOR CRANIAL FLAP

(71) Applicant: VITALYS SURGICAL, Vitre (FR)

(72) Inventor: Pierre-Yves Collerais, Vitre (FR)

(73) Assignee: Vitalys Surgical, Vitre (FR)

( * ) Notice: Subject to any disclaimer, the term of this patent is extended or adjusted under 35 U.S.C. 154(b) by 350 days.

(21) Appl. No.: 16/984,676

(22) Filed: Aug. 4, 2020

(65) Prior Publication Data

US 2021/0038265 A1 Feb. 11, 2021

(30) Foreign Application Priority Data

Aug. 6, 2019 (FR) ...................................... 1909023

(51) Int. Cl.
*A61B 17/68* (2006.01)
*A61B 17/00* (2006.01)

(52) U.S. Cl.
CPC .. *A61B 17/688* (2013.01); *A61B 2017/00367* (2013.01); *A61B 2017/681* (2013.01)

(58) Field of Classification Search
CPC .. A61B 17/68; A61B 17/688; A61B 2017/681
See application file for complete search history.

(56) References Cited

U.S. PATENT DOCUMENTS

| | | | |
|---|---|---|---|
| 5,449,361 A | 9/1995 | Preissman | |
| 6,379,363 B1 * | 4/2002 | Herrington | ........ A61B 17/8863 606/104 |
| 6,921,401 B2 * | 7/2005 | Lerch | ................... A61B 17/688 606/232 |
| 8,920,095 B2 * | 12/2014 | Baugh, Sr. | .............. F16B 19/00 411/512 |
| 9,034,020 B2 * | 5/2015 | Knopfle | ............... A61B 17/688 606/282 |
| 9,433,438 B2 * | 9/2016 | Memmolo | ........... A61B 17/688 |
| 9,622,784 B2 * | 4/2017 | Memmolo | ........... A61B 17/688 |

(Continued)

FOREIGN PATENT DOCUMENTS

| | | |
|---|---|---|
| DE | 202007007880 U1 | 8/2007 |
| DE | 102007026079 B3 * | 9/2008 ........... A61B 17/688 |

(Continued)

OTHER PUBLICATIONS

French Search Report for FR1909023 dated May 20, 2020.

*Primary Examiner* — Eric S Gibson
(74) *Attorney, Agent, or Firm* — Thomas Horstemeyer, LLP

(57) ABSTRACT

A fixator of a cranial flap to a skull, the fixator comprising a rigid rod, a lower disk placed at a distal extremity of said rigid rod, an upper disk mounted so as to be mobile along said rigid rod and a grip connected to the proximal extremity of said rigid rod enabling said upper disk to be made to slide towards said lower disk, said distal extremity of said rigid rod being provided with a ball-joint element and said lower disk comprising a recess for receiving said ball-joint element; said lower disk and said upper disk have convex shapes and are made out of a material enabling them to get deformed and adapt to shapes of the skull and the cranial flap, the lower and upper disks are placed flat against and secured to the internal and external surfaces of the skull and of the cranial flap.

9 Claims, 3 Drawing Sheets

(56) References Cited

U.S. PATENT DOCUMENTS

| | | | | |
|---|---|---|---|---|
| 2002/0016593 A1* | 2/2002 | Hearn | A61B 17/688 | 606/916 |
| 2002/0156475 A1* | 10/2002 | Lerch | A61B 17/688 | 606/70 |
| 2002/0169455 A1* | 11/2002 | Bannerman | A61B 17/688 | 606/99 |
| 2003/0036760 A1* | 2/2003 | Yeh | A61B 17/688 | 606/71 |
| 2003/0229349 A1* | 12/2003 | Wellisz | A61B 17/688 | 606/151 |
| 2004/0034375 A1* | 2/2004 | Ruiz | A61B 17/688 | 606/151 |
| 2004/0127908 A1* | 7/2004 | Roman | A61B 17/688 | 606/328 |
| 2005/0137608 A1* | 6/2005 | Hearn | A61B 17/688 | 606/103 |
| 2006/0064110 A1* | 3/2006 | Nesper | A61B 17/688 | 606/105 |
| 2008/0275511 A1* | 11/2008 | Weinacker | A61B 17/8869 | 606/60 |
| 2010/0094362 A1* | 4/2010 | Lutze | A61B 17/8869 | 606/86 R |
| 2010/0305619 A1* | 12/2010 | Knopfle | A61B 17/688 | 606/282 |
| 2013/0110181 A1* | 5/2013 | Piotrowski | A61B 17/8869 | 606/324 |
| 2014/0072386 A1* | 3/2014 | Baugh, Sr. | F16B 21/073 | 411/337 |
| 2014/0135852 A1* | 5/2014 | Memmolo | A61B 17/688 | 606/324 |
| 2015/0080975 A1* | 3/2015 | Pleil | A61B 17/808 | 606/86 R |
| 2021/0038265 A1* | 2/2021 | Collerais | A61B 17/688 | |

FOREIGN PATENT DOCUMENTS

| | | | | |
|---|---|---|---|---|
| DE | 202008013320 U1 * | 1/2009 | | A61B 17/688 |
| DE | 102008050870 A1 * | 4/2010 | | A61B 17/688 |
| DE | 102008050870 A1 | 4/2010 | | |
| EP | 3772346 A1 * | 2/2021 | | A61B 17/688 |
| EP | 3772346 B1 * | 5/2022 | | A61B 17/688 |
| FR | 3099694 A1 * | 2/2021 | | A61B 17/688 |
| WO | 2004/089231 A1 | 10/2004 | | |
| WO | 2004089231 A1 | 10/2004 | | |
| WO | WO-2008145307 A1 * | 12/2008 | | A61B 17/688 |

* cited by examiner

FIXATOR FOR CRANIAL FLAP

CROSS-REFERENCE TO RELATED APPLICATION

This application claims the priority to and benefit of French Patent Application No. 1909023, filed Aug. 6, 2019, which is herein incorporated by reference in entirety.

TECHNICAL FIELD

The present invention relates to the field of implantable surgical devices.

More specifically, the present technique relates to surgical devices classically used by neurosurgeons during operations/procedures of craniotomy/craniectomy in order to reposition and fix a cranial flap that has been preliminarily removed in order to open out a surgical approach and treat a pathology.

Such devices are usually called cranial flap fixators and are intended to position and hold the cranial flap in place within the cranial orifice, subsequently to the surgical operation/procedure treating the pathology.

PRIOR ART

Cranial flap fixators are widely used to position and hold in position, within a cranial orifice, a cranial flap that has previously been removed during a craniotomy. Their use is generally reliable and relatively easy for the surgeon. In general, three or four fixators are used on a same cranial flap to cooperate with respectively three or four perforations previously made by means of a cranial perforator.

Each cranial flap fixator generally comprises a lower disk that is to be placed by hand by the surgeon beneath the periphery of the cranial orifice between the dura-mater and the internal surface of the cranial bone, here below called the skull. When the lower disk of each fixator is positioned and when the cranial flap is repositioned in the cranial orifice, an upper disk can be brought into contact against the upper surfaces of the cranial bone and of the cranial flap. The lower and upper disks of each fixator are then compressed against each other in order to hold the cranial flap in position in the cranial orifice.

Once the disks are positioned, a rigid rod of the fixator has to be sectioned at a position flush with the upper disk, using a cutting clamp.

In particular, such fixators are commercially distributed by the firm Aesculap AG under the trade name CranioFix®2.

One drawback of this technique lies in the fact that the titanium used to manufacture the fixator produces artifacts or even a shadow zone during the examinations by radiation (MRI, scanner, x-rays, etc.) that have to be carried out in post-operational conditions.

Another drawback of this technique lies in the fact that the different specific instruments used must be sterilized before each use.

A second technique, commercially distributed under the name "Cranial Loop" by the firm NEOS Surgery S. L., proposes to fixedly attach the lower and upper disks by means of two flexible rods made out of a polymer material for example. These fixators are provided with a one-time-use grip in the form of a loop which makes it possible to shift the upper disk along flexible rods towards the lower disk. The flexible rods are then sectioned flush with the upper disk, this disk being folded two or three times.

One drawback of this technique lies in the fact that, during its use, the surgeon needs both hands to apply the fixator properly. The "application of the fixator" is understood to mean the compression of the lower and upper disks against the cranial flap. More specifically, the tool takes the form of a grasping loop, of which each extremity is connected to one of the flexible rods. To apply the fixator, the surgeon must therefore hold the upper disk with one hand and pull on the grasping loop with the other hand in order to shift the upper disk towards the lower disk. The surgeon therefore needs both hands to implement the fixator, and this is unsatisfactory.

It can be noted that for each of these techniques, the excess part of the rod must be cut off. For the second technique, it is therefore necessary to cut off the extremities of both flexible rods, and this requires additional operation time on the part of the surgeon, and this is the case for each fixator.

Another technique commercially distributed under the name "Aesculap CranioFix® Absorbable" by the firm Aesculap AG consists in manufacturing the lower and upper disks out of an absorbable material such as polyester so that the fixator itself gets absorbed after a certain number of weeks. According to this technique, the disks are connected to each other by a plurality of suture threads.

This technique in which absorbable fixators are implemented is particularly suited to pediatrics to avoid hindering or jeopardizing the growth of the child's skull. However, absorbable fixators are not generally recommended for adults. In addition, the fixed attachment of the lower and upper disks by suture requires once again that the surgeon use both hands. Finally, it will be noted that the lower and upper disks must have a substantial thickness resulting from the absorbable nature of the material that composes them.

It is observed in addition that, in practice, it is often difficult for the neurosurgeon to accurately position the lower disk against the internal wall of the skull. Indeed, this wall may have anatomical over-thicknesses or hollows resulting from the craniectomy. Since the lower disk is imperfectly positioned, the upper disk is also imperfectly positioned owing to the rigidity of the design. It can happen that the lower and upper disks are thus not parallel to each other and may be misaligned. This wrong positioning can lead to defects in the healing process and therefore to complications that can have harmful effects for the patient.

To try and resolve this problem, there is a fixator known from DE102008050870A1. The rod of this fixator is connected to the lower disk so as to enable a tilting of the rod relative to the lower disk and thus improve the positioning of this disk. However, this solution is not completely satisfactory because it implements disks made of titanium or some other rigid material. This rigidity of the disks prevents an optimized positioning of the lower disk and, as a corollary, an optimized positioning of the upper disk so as to perfectly adapt the fixator to the anatomy of the internal wall and therefore that of the external wall of the skull.

Disks made of titanium or any other rigid material have in addition the drawback of protruding from the surface of the skull. They are indeed manufactured by press stamping and therefore have a certain thickness related to their shape. After the scalp is repositioned, the upper disks form bumps that are visible and detectable to touch, constituting a source of physical and psychological discomfort for the patient and even causing esthetic impairment. The lower disks for their part protrude from the internal surface of the skull, giving rise to problems of tolerance.

There is therefore a need for a cranial flap fixator enabling the optimized positioning of its disks for perfect adaptation to the anatomy of the internal and external walls of the skull.

There is also a need for a fixator, of which the upper disk once covered with the scalp does not form any bump and is undetectable, whether visually or by touch.

There is therefore a need for a fixator of this kind that is simpler to handle than the prior-art fixators.

SUMMARY OF THE INVENTION

The present technique can be used to resolve at least some of the drawbacks raised by the prior art. The present technique indeed refers to a cranial flap fixator comprising a rigid rod, a lower disk placed at a distal extremity of said rigid rod, an upper disk mounted so as to be mobile along said rigid rod and a grip connected to the proximal extremity of said rigid rod enabling said upper disk to be made to slide towards said lower disk, said distal extremity of said rigid rod being provided with a ball-joint element hinged in a recess and said lower disk comprising a recess for receiving said ball-joint element.

According to the proposed technique, said lower disk and said upper disk have convex shapes and are made out of a material that enables them to get deformed so as to match the shapes of the skull and the cranial flap so that, after application, the lower and upper disks are placed flat against and secured to the internal and external surfaces of the skull and of the cranial flap, the disks and the skull then being contained within a same profile. They thus perfectly match the shape of the skull without extending beyond it ("profile 0").

According to the invention, the rigid rod is hinged in the recess of the lower disk so as to allow a tilting of the rigid rod relative to the lower disk. Thus, the lower disk can adapt to the internal surface of the skull and to the internal surface of the cranial flap. This polyaxial character of the rigid rod makes it possible to position the lower disk as efficiently as possible relative to the internal surface of the skull and the cranial flap. In addition, the shape and material of the disks permit their deformation. This deformation enables the disks, during their application, to be placed flat against and secured respectively to the internal and external surfaces of the skull and the cranial flap, so that they can get completely adapted to these surfaces. Thus, after the positioning of these disks, the lower disk forms no bump and, once covered with the scalp, forms no protrusion that can be detected visually or by touch, providing the patient with greater comfort. Since the lower disk coincides with the internal surface of the skull, it interacts less with the tissues underlying it, thus improving its tolerance and reducing the risks of complication at this level.

Thus, the positioning of the lower disk and the upper disk can be improved and therefore proves to be more efficient than that obtained with prior-art devices. The fixator according to the invention is therefore more reliable than those of the prior art in that its use is liable to reduce the risks related to imperfect positioning of the disks and, in addition, contributes to better tolerance of these disks.

The proposed technique provides a solution that is easy to use, requiring no instrument set and no instrument to accompany the positioning of the implant.

In one particular embodiment, said lower disk and said upper disk of the fixator each have a plurality of petals extending on their periphery. Such petals, with the material constituting the disks, contribute to the flexibility of these disks enabling their deformation when they are applied.

Such a shaping in petal form procures a deformation of the disks that is radially variable from one petal to another and thus improves the matching of these disks to the anatomical shape of the internal and external surfaces of the skull.

According to one particular aspect, the disks and the rigid rod are made out of a biocompatible and biostable material that produces no artifact during examinations by radiation. It is thus radio-transparent and resistant.

Thus, the disks and the rigid rod are manufactured out of a material perfectly suited to being implanted in the human body without producing any harmful effect in the patient.

According to one particularly interesting aspect, the disk and the rod are manufactured out of the Peek Optima® material (registered mark).

Such a material has the advantage of being biocompatible and biostable and producing no artifacts during examinations by radiation.

According to one variant of the invention, said ball-joint element and said recess are configured to allow a tilting, and therefore a polyaxial character of the rigid rod, relative to a longitudinal plane of the lower disk by an angle that can vary between 0° and 20°.

Such an angle of tilt makes it easy to insert the lower disk beneath the skull when positioning the fixator. This angle also makes it possible to optimally position the lower disk during the application/compression of the fixator.

According to one particular aspect, said rigid rod is a rack device and said upper disk has at least two or preferably four jaws, each of said jaws being provided with at least one or preferably two pins designed to cooperate with the notches of said rack device.

Thus, the upper disk can shift solely towards the lower disk. Indeed, the at least one pin (it can be planned for example to have two pins) and the rack device are configured to enable a shifting of the upper disk towards the lower disk and prevent a shifting of the upper disk in a direction opposite to the lower disk. This relatively simple technical solution enables the automatic locking of the position of the upper disk on the rigid rod.

According to one particular aspect, said lower disk is fixed to said distal extremity of said rigid rod.

In this way, only the upper disk can shift along the rigid rod. The mechanism is therefore relatively reliable and simple to implement.

According to one particular aspect, said grip has a hollow cylindrical element provided with two grasping fins and a piston sliding in said hollow cylindrical element.

In this way, the grip can be handled with only one hand. The surgeon can hold the grip with two fingers (the middle finger and the index for example) positioned beneath the fins and at the same time press the piston with the thumb of the same hand. The handling of such a grip is similar to the handling of a syringe.

According to another particular aspect, said hollow cylindrical element comprises means for fixedly attaching said proximal extremity of said rigid rod.

In this way, the grip to which said rigid rod is affixed during the application of the fixator can be easily detached from the rigid rod after the compression of the disks against the cranial flap and the skull.

According to yet another particular aspect, said means for fixedly attaching have a tapped hole cooperating with a threaded portion of said proximal extremity of said rigid rod.

Once the grip has been actuated to bringer the disks closer to each other and compress them against each other, the grip can be easily removed. To this end, it is enough to raise it along the rod to release the rod. The rigid rod can then be sectioned at a position flush with the disk.

According to another aspect, said grip is a one-time-use grip. It can thus advantageously be made out of a rigid plastic material. It can also for example be manufactured out of acrylonitrile butadiene styrene (ABS).

In this way, all health risks are limited. Indeed, the fixator is provided as a single element in which the rigid rod is directly fixed to the grip. The unit is stored in a sterilized package so that the surgeon can use it in a reliable way.

LIST OF FIGURES

Other features and advantages of the invention shall appear more clearly from the following description of a preferred embodiment, given by way of a simple illustrative and non-exhaustive example, and from the appended figures of which:

DETAILED DESCRIPTION OF THE INVENTION

Structure of the Fixator

The general principle of the proposed technique relies on the combination of the implementing of disks deformable on their external peripheries and a ball-type link with a polyaxial character at the level of the junction between the lower disk and the rod of the fixator. The proposed technique also relies on the implementing of a grip enabling the use of the fixator with only one hand.

Figure 1:
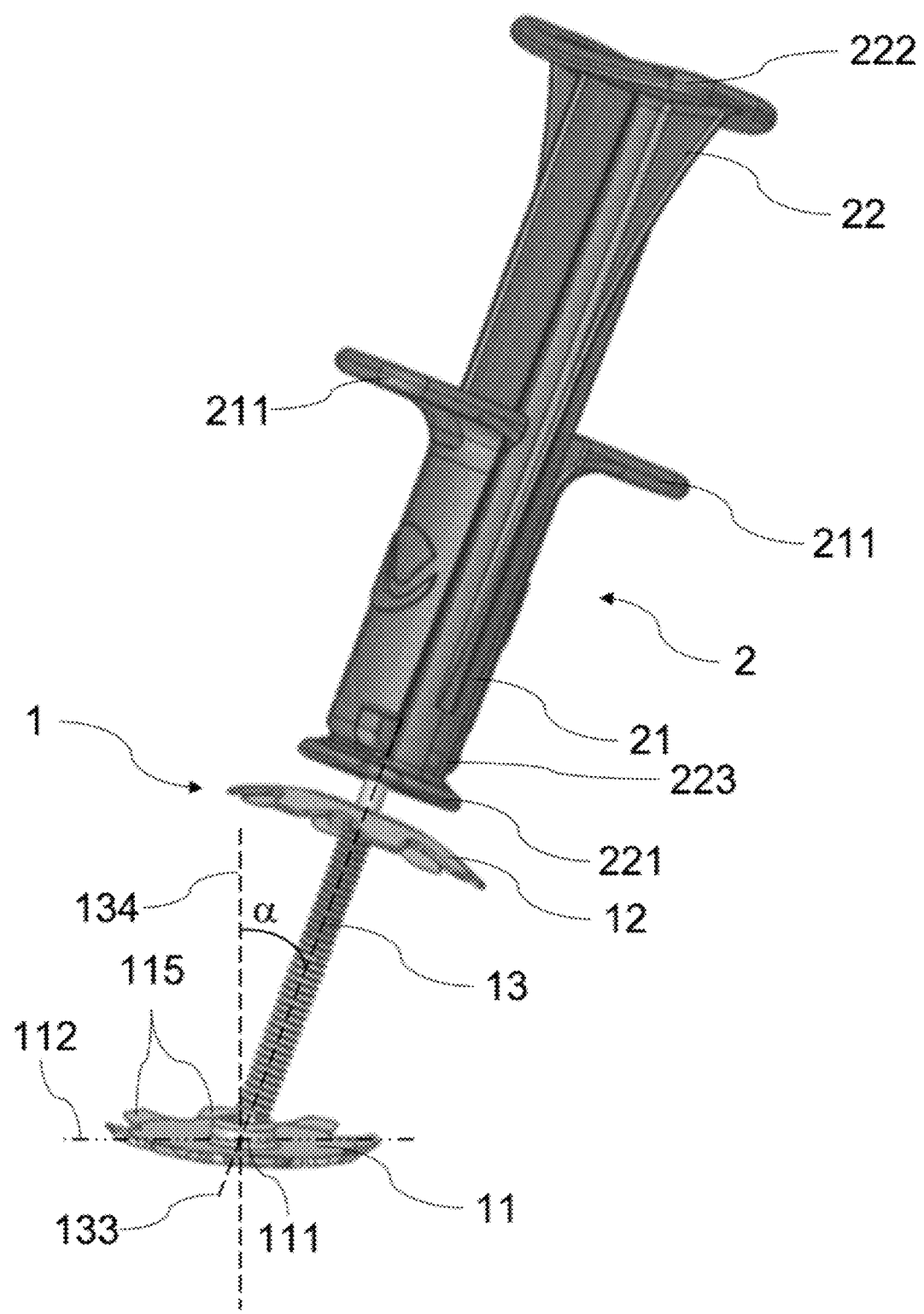
FIG. 1 is a view in perspective or a three-quarter view of a fixator according to the proposed technique in its initial position.
Figure 2:
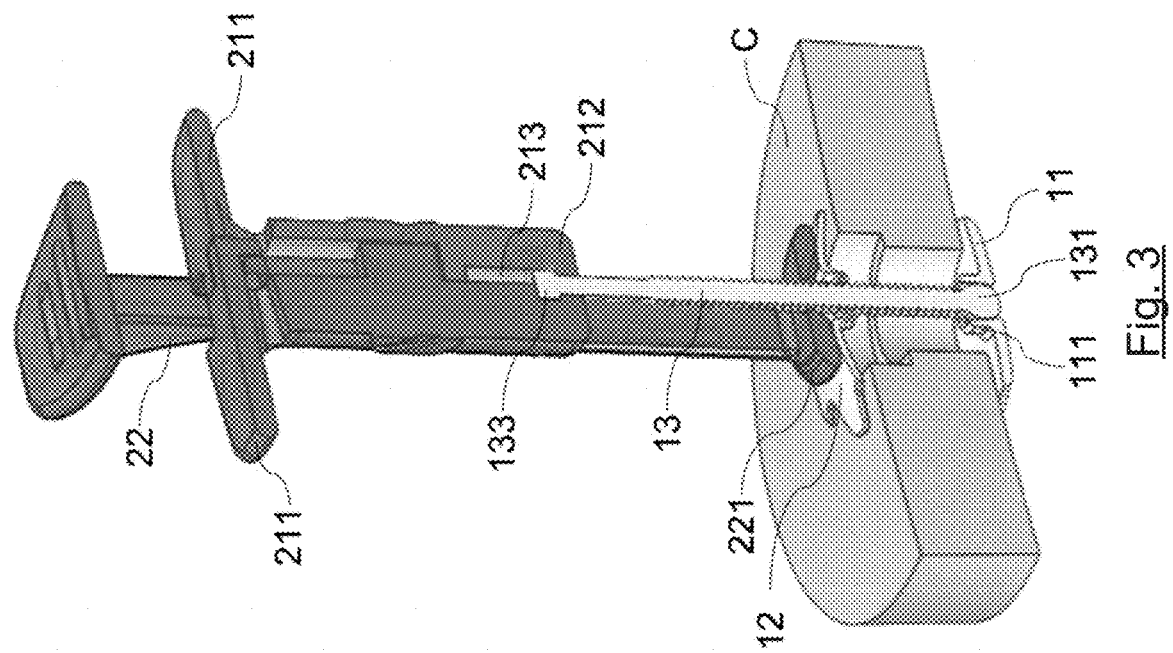
FIG. 2 illustrates a cross-section view of the fixator of FIG. 1 when it is implemented against a cranial flap.
Figure 3:
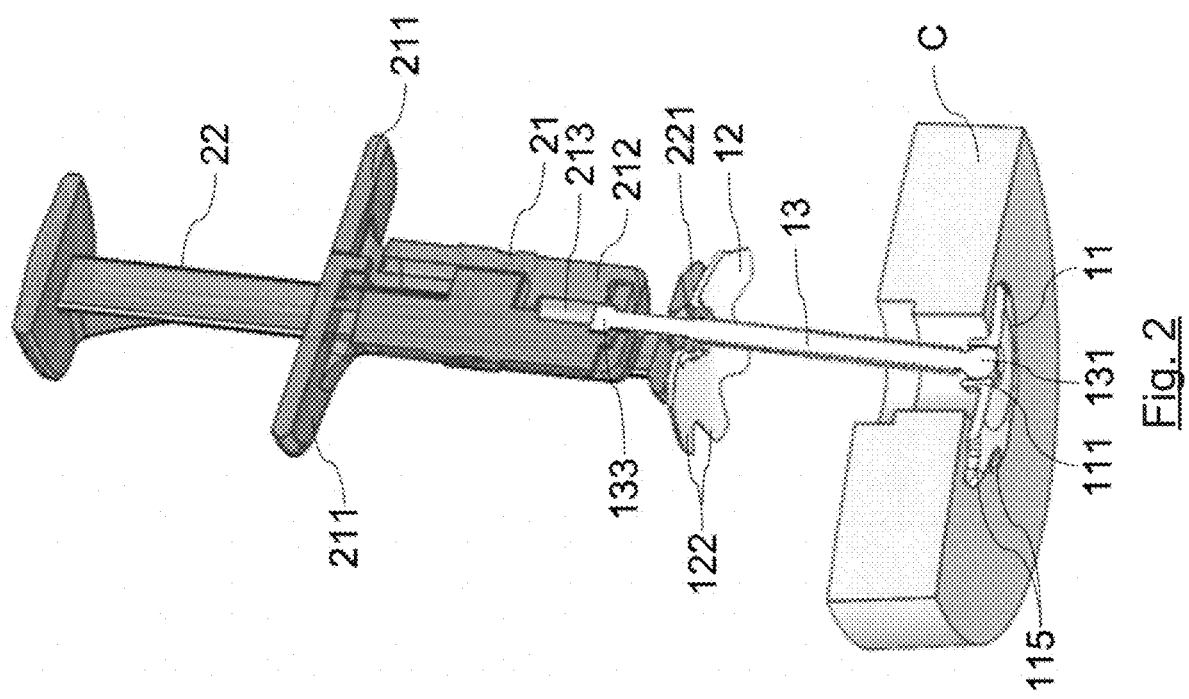
FIG. 3 illustrates a cross-section view of a fixator according to the proposed technique in an intermediary position, when it is being implemented against a cranial flap.

FIGS. 1 to 3 illustrate a fixator 1 according to the invention.

As illustrated in FIG. 1, the fixator 1 comprises a lower disk 11 that substantially takes the form of a disk. An upper disk 12, also disk-shaped, is mounted slidingly along a rigid rod 13, the distal extremity of which is fixed to the lower disk 11. The fixator also comprises a grip 2.

The lower disk 11 and upper disk 12 are slightly convex before being applied to the fixator 1 and have a plurality of petals 115, 122 extending on the periphery of the disk.

The convex shape of the disks 11 and 12 and the material out of which they are made enables them to get slightly deformed so that the petals 115, 122 adapt to the shapes of the skull and of the cranial flap C. Thus, after application, the disks 11, 12 are optimally placed flat against/secured to the internal and external surfaces of the skull and of the cranial flap C. Thus, the disks and the skull are inscribed within the same profile.

As illustrated in FIGS. 2 and 3 especially, the distal extremity of the rigid rod 13 is fixed to the lower disk 11. More specifically, this extremity of the rigid rod 13 has a ball-joint element 131. The lower disk 11 presents, substantially at its center, a groove or recess 111 shaped to receive and hold the ball-joint element 131 of the rigid rod 13. The recess 111 has an appreciably circular shape. The ball-joint element 131 and the recess 111 enable the rigid rod 13 to get tilted relative to the longitudinal plane 112 of the lower disk 11. More specifically, the rigid rod 13 can tilt by an angle a ranging from 0° to 20° about an axis 134 extending perpendicularly to the longitudinal plane 112 of the lower disk 11, the axis 134 preferably passing through the center of the lower disk 11. The ball-joint element 131 and the recess 111 give the rigid rod 13 a polyaxial character relative to the lower disk 11.

It will be also noted that neither the ball-joint element 131 nor the recess 111 protrude from the external surface of the lower disk. On the contrary, this recess 111 is planned to be entirely on the inner concave side of the lower disk, and the ball-joint element received by this recess is therefore itself positioned on this concave side.

The rigid rod 13 more particularly takes the shape of a rack device. In other words, the external surface of the rigid rod 13 has a plurality of regular notches 132. For example, the notches 132 have an appreciably triangular shape.

Figure 5:
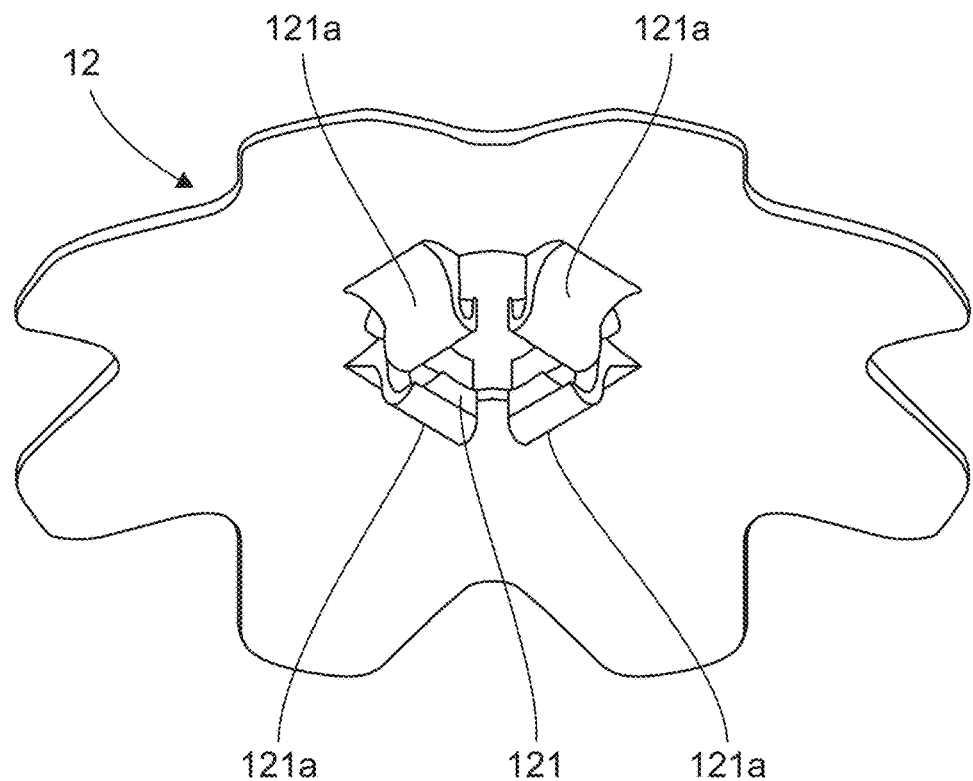
FIG. 5 illustrates a lower perspective view or three-quarter view of the upper disk of the fixator shown in FIGS. 1 to 4.

Referring to FIG. 5, the upper disk 12 comprises, at its center, an aperture/hole enabling the passage of the rigid rod 13. More particularly, the aperture has four jaws 121a each provided with two pins 121 for cooperating with the notches 132 of the rack device.

It will be noted that the neither the jaws 121a nor the pins 121 of these jaws protrude out of the external surface of the upper disk. On the contrary, this jaw 121a and these pins 121 are planned to be entirely on the internal concave side of the upper disk.

In this example, four jaws 121a, each provided with two teeth extending over the entire periphery of the aperture for the passage of the rod, are planned. In one variant, a different number of jaws or a different number of pins could be implemented on the periphery of this aperture.

The notch 132 of the rack device and the pin 121 are configured to enable a movement/sliding of the upper disk 12 along the rigid rod 13 towards the lower disk 11. In addition, the notches 132 of the rack device and the pin 121 are configured to prevent the upper disk 12 from moving away from the lower disk 11. In other words, the notches 132 of the rack device and the pin 121 prevent a movement of the upper disk 12 in a direction opposite/inverse to that of the lower disk 11.

When the disks are applied, it is therefore simply necessary to shift/bring the upper disk 12 closer towards the lower disk 11. In other words, no additional action/handling is necessary to lock the position of the upper disk 12 to the rigid rod 13. Indeed, the shifting of the upper disk in a direction opposite that of the lower disk 11 is not permitted by the mechanism comprising the rack device and the pin 121.

According to the proposed technique, the fixator 1 has a one-time-use grip 2 or applicator. This grip enables the surgeon to apply the disk with only one hand.

The grip 2 has a hollow cylindrical body, or element, 21 having two grasping fins 211 that enable the surgeon to hold the grip 2 with two fingers (the middle finger and the index for example). The fins 211 also make it possible to pull the rigid rod 13 and hence the lower disk 11 in order to accurately place the lower disk 11 flat against the internal surface of the skull and of the cranial flap C.

The grip 2 furthermore has a sliding piston or push-rod 22 passing through the hollow body 21. The piston 22 is diskable of sliding in the hollow body 21 when a force is applied by the surgeon on its upper extremity 222 taking appreciably the form of a push-button.

The lower extremity 223 of the piston 22 has a supporting element 221 in the shape of a thin washer intended to come into contact with the upper disk 12. Thus, when the piston 22 is shifted in the cylindrical hollow body 21, the supporting element 221 comes into contact with the upper disk 12 and pushes/shifts this disk towards the lower disk 11 as illustrated in FIGS. 2 and 3. It will be noted that the washer-shaped supporting element 221 has a diameter wider than the diameter of the perforations made during craniectomy. In practice, the diameter will be advantageously 17 mm while the perforations in the adult skull have a diameter of at most 14 mm. Thus, during the use of the fixator according to the invention by the neurosurgeon who will use the grip to compress the disks, this washer-shaped supporting element will, in a position of maximum compression, rest largely on the top of the upper disk without any risk of making it collapse at its center. Thus, the neurosurgeon will be able to evaluate the successful execution of this step not only by a visual check but also by an auditory and tactile check.

During use, the neurosurgeon holds the grip 2 with two fingers on the fins 211 and pushes the piston 22 through the push-button 222 with his thumb for example. Thus, he brings the push-button 22 closer to the fins 213, and this brings the lower disk 11 and upper disk 12 closer to each other until the disks 11 and 12 are compressed against the skull and the cranial flap C.

The hollow cylindrical body 21 furthermore comprises means 212 for fixedly attaching the proximal extremity of the rigid rod. These means make it possible to hold the rigid rod 13 when the upper disk 12 is shifted towards the lower disk 11 during the application of the fixator 1.

In this example, the proximal extremity of the rigid rod 13 has a threaded portion 133 intended to cooperate with a tapped hole 213 made in the fixedly attaching means 212 of the cylindrical hollow body 21. The fixator 1 and the grip 2 can therefore be fixedly attached/detached by screwing/unscrewing.

It will be understood naturally that other solutions can be envisaged to fixedly attach the rigid rod 13 to the grip 2. For example, it is possible to provide a clip-on/clipping system or a pin-based system.

The fixator, including its grip, is advantageously a one-time-use device so as to do away with any health risks when it is being used.

The fixator 1 is preferably made out of a biocompatible and biostable material so as to reduce the risks of rejection by the patient's body and thus reduce complications following the procedure.

In addition, the material used to manufacture the fixator is preferably a material that produces no artifacts under examination by radiation (MRI, scanners, or x-rays for example).

Preferably, the fixator is made out of the PEEK OPTIMA® (registered mark) material. This special material has the advantage of being biocompatible and biostable and of not producing any artifacts during examination under rays.

Use of the Fixator

Figure 4:
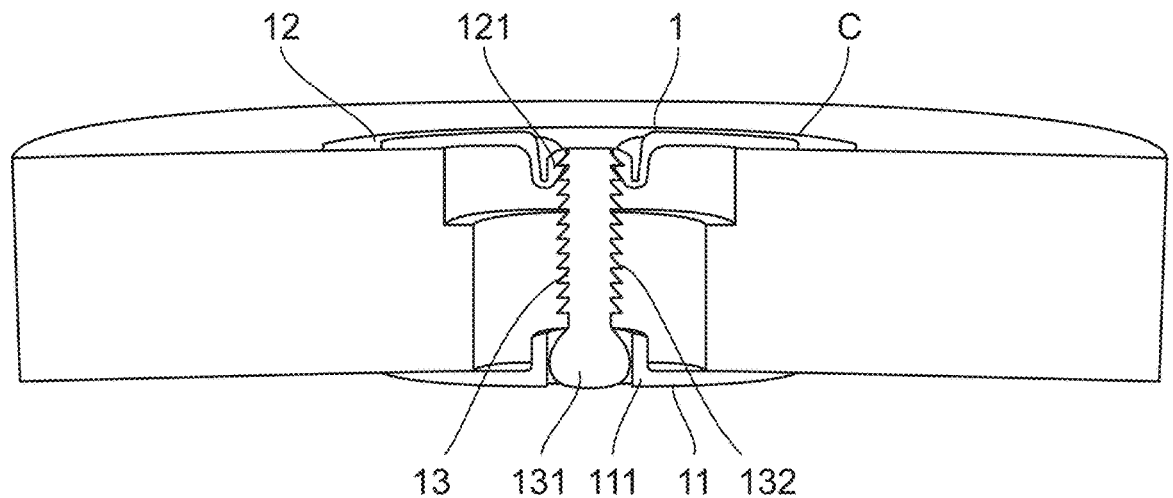
FIG. 4 illustrates a cross-section view of a fixator according to the proposed technique in a final position, when it is implemented against a cranial flap.

The fixator 1 of the proposed technique is intended to fix a cranial flap C, which can be seen in FIGS. 2 to 4, within a cranial orifice (not shown) during a craniotomy. More specifically, several fixators are implemented to fix the cranial flap C. Their number depends on the dimensions of the cranial flap C in particular.

Thus, to affix a cranial flap C, it is necessary to place several fixators 1 on the periphery of the cranial orifice depending on the number of trepanations. More specifically, for each fixator 1, the lower disk 11 should be inserted/placed within the skull, between the dura-mater and the internal surface of the skull. The cranial flap C can then be put back into place within the cranial orifice.

The ball-joint element 131, at this stage, enables a tilting of the rigid rod 13 so as to optimize the positioning of the lower disk 11 against the internal surface of the skull and the internal surface of the cranial flap C as illustrated in FIG. 2. The internal surfaces are the surfaces within the skull, i.e. oriented towards the patient's brain.

When the cranial flap C is accurately positioned in the cranial orifice, the upper disk 12 must be put into contact and compressed against the external surface of the skull and the external surface of the cranial flap C. To this end, it is enough for the surgeon to grasp the grip 2 of the fixator 1 and push on the piston 22. More specifically, the surgeon can carry out this operation with only one hand. Indeed, it is enough for him to hold the grip 2 with two fingers (the index and the middle finger for example) through the grasping fins 211 and press/push on the piston 2 with his thumb for example.

The application of a force to the piston 22 causes a shifting of the piston 22 towards the cranial flap C. This shifting of the piston 2 thus causes a shifting of the upper disk 12 along the rigid rod 13 towards the lower disk 11. In other words, the grip 2 can be used relatively similarly to a syringe, and this proves to be simple and efficient for the surgeon. The grip 2 of the proposed technique thus makes it possible to shift the upper disk 12 in requiring the use of only one hand by the surgeon, and this facilitates the application of the fixator 1. This application is further facilitated by the fact that the embodiment of the fixator presented herein is very light and weighs only about five grams.

The shifting of the piston 22 and therefore of the upper disk 12 is done until the upper disk 12 is compressed against the upper surface of the cranial flap C as illustrated in FIG. 3. During the shifting of the upper disk 12 on the rigid rod 13, the pin 121 crosses the notches 132 of the rack device one by one in moving towards the lower disk 11. A shifting of the upper disk 12 in the reverse direction is prevented by the particular shape of the notches 132 and of the pin 121 as described here above.

During the compression of the lower disk 11 and upper disk 12 against the cranial flap C and the skull, the rigid rod 13 recovers/resumes a perpendicular orientation relative to the longitudinal plane 112 of the lower disk 11. The ball-joint element 131 therefore does not enable a tilting of the rigid rod 13 except during the affixing of the fixator 11. When the fixator 11 is applied, i.e. when it is in its intermediate position (FIG. 3) or final position (FIG. 4), the rigid rod 13 is no longer tilted relative to the lower disk 11. The lower disk 11 and upper disk 12 therefore extend substantially in parallel relative to each other.

During the compression of the lower disk 11 and upper disk 12 against the cranial flap C and the skull, the disks get deformed slightly to completely adapt to their external and internal surfaces. The disks, the cranial flap and the skull are then contained within a same profile.

Since the supporting element 221 of the piston 22 has a size greater than that of the perforations made during the craniectomy, the upper disk cannot be crushed and compressed beyond the surface of the skull when the neurosurgeon actuates the piston, and this makes his procedure safe. The fact that this supporting element 221 goes beyond either side of the perforation of the skull is therefore highly reassuring for the neurosurgeon.

In particular, the upper disk 12, once covered with the patient's scalp, forms no bump that can be detected visually or by touch. The lower disk for its part has practically no protrusion towards the interior of the skull, and this thus protects the underlying tissue such as the dura-mater.

Once the lower disk 11 and upper disk 12 are compressed against the skull and the cranial flap C, the grip 2 can be easily removed. The rod thus removed can then be sectioned by means of a cutting clamp at a level flush with the upper disk.

After the fixator 1 has been detached from the grip 2, the excess portion of the rigid rod 13 extending beyond the upper disk 12 can be cut off, as illustrated in FIG. 4. The term "excess portion" is understood to mean the portion of the rigid rod 13 extending between the upper disk 12 and the proximal extremity having the threaded portion 133 of the rigid rod 13. In other words, the rigid rod 13 is cut off flush with the upper disk 12.

The invention claimed is:

1. A fixator of a cranial flap to a skull having at least one perforation, the fixator comprising a rigid rod, a lower disk placed at a distal extremity of said rigid rod, an upper disk mounted so as to be mobile along said rigid rod and a grip connected to a proximal extremity of said rigid rod enabling said upper disk to be made to slide towards said lower disk, said distal extremity of said rigid rod being provided with a ball-joint element and said lower disk comprising a recess for receiving said ball-joint element, said lower disk and said upper disk having convex shapes;

characterized in that said lower disk and said upper disk are made out of a material enabling them to get deformed so as to adapt to shapes of the skull and the cranial flap in such a way that, after application, the lower and upper disks are placed flat against and secured to internal and external surfaces of the skull and of the cranial flap, the disks and the skull then being contained within a same profile;

and in that said grip has a hollow cylindrical element provided with two grasping fins and a piston sliding in said hollow cylindirical element, said piston having an upper extremity forming a push-button configured to adapt to a thumb of a surgeon and a lower extremity having a supporting element in the shape of a thin washer intended to come into contact with the upper disk.

2. The fixator according to claim 1 characterized in that said lower disk and said upper disk each have a plurality of petals extending on their periphery.

3. The fixator according to any one of the claim 1, characterized in that said fixator is manufactured out of a biocompatible and biostable material that produces no artifact under examinations by radiation.

4. The fixator according to any one of the claim 1, characterized in that said ball-joint element and said recess are configured to allowing a tilting of the rigid rod relative to a longitudinal plane of the lower disk by an angle that can vary between 0° and 20°.

5. The fixator according to claim 1, characterized in that said rigid rod is a rack device and in that said upper disk has at least two jaws, each of said jaws being provided with at least one pin designed to cooperate with notches of said rack device.

6. The fixator according to any one of the claim 1, characterized in that said lower disk is fixed to said distal extremity of said rigid rod.

7. The fixator according to any one of the claim 1, characterized in that said hollow cylindrical element comprises an attachment portion adapted to fixedly attach said proximal extremity of said rigid rod.

8. The fixator according to claim 7, characterized in that said attachment portion has a tapped hole cooperating with a threaded portion of said proximal extremity of said rigid rod.

9. The fixator according to any one of the claim 1, characterized in that the fixator is a one-time-use fixator.

\* \* \* \* \*